(12) United States Patent
Schenker et al.

(10) Patent No.: US 10,689,435 B2
(45) Date of Patent: Jun. 23, 2020

(54) THERAPY AND PROPHYLAXIS OF INFECTIOUS DISEASE CAUSED BY ZIKA VIRUS

(71) Applicant: KAMADA LTD., Ness Ziona (IL)

(72) Inventors: Eran Schenker, Tel Aviv (IL); Yuval Sagiv, Gedera (IL)

(73) Assignee: KAMADA LTD., Ness Ziona (IL)

( * ) Notice: Subject to any disclaimer, the term of this patent is extended or adjusted under 35 U.S.C. 154(b) by 0 days.

(21) Appl. No.: 16/118,847

(22) Filed: Aug. 31, 2018

(65) Prior Publication Data
US 2018/0371063 A1 Dec. 27, 2018

Related U.S. Application Data

(63) Continuation-in-part of application No. PCT/IL2017/050243, filed on Feb. 27, 2017.

(60) Provisional application No. 62/302,842, filed on Mar. 3, 2016, provisional application No. 62/695,061, filed on Jul. 8, 2018.

(51) Int. Cl.
| | |
|---|---|
| *C07K 16/10* | (2006.01) |
| *A61K 39/42* | (2006.01) |
| *A61K 39/12* | (2006.01) |
| *A61P 31/14* | (2006.01) |
| *A61K 39/00* | (2006.01) |

(52) U.S. Cl.
CPC .............. *C07K 16/10* (2013.01); *A61K 39/12* (2013.01); *A61K 39/42* (2013.01); *A61P 31/14* (2018.01); *C07K 16/1081* (2013.01); *A61K 2039/505* (2013.01); *A61K 2039/545* (2013.01); *A61K 2039/55* (2013.01); *C07K 2317/76* (2013.01)

(58) Field of Classification Search
CPC .. C07K 16/10; C07K 10/1081; C07K 317/76; A61P 31/14; A61K 39/12; A61K 39/49; A61K 2039/545; A61K 2039/55
See application file for complete search history.

(56) References Cited

U.S. PATENT DOCUMENTS

2011/0150904 A1 6/2011 Schiltz et al.

OTHER PUBLICATIONS

Summers et al. Journal of Travel Medicine 2015, vol. 22, issue 5, pp. 338-340.*
Lanciotti et al. Emerg. Infect. Dis. Aug. 14, 2008 (8), 1232-1239.*
The SAFE Study Investigators (N Engl. J. Med. 2004, vol. 350, pp. 2247-2256).*
Giovanni, N., et al., "Passive Immunization during Pregnancy for Congenital Cytomegalovirus Infection," The New England Journal of Medicine, vol. 353, pp. 1350-1362 (Sep. 29, 2005).
Sapparapu, G., et al., "Neutralizing Human Antibodies Prevent Zika Virus Replication and Fetal Disease in Mice," Nature, vol. 540, pp. 443-447 (Dec. 15, 2016).
International Search Report of PCT/IL2017/050243 dated Jun. 6, 2017.
Written Opinion of PCT/IL2017/050243 dated Jun. 6, 2017.

* cited by examiner

*Primary Examiner* — Bao Q Li
(74) *Attorney, Agent, or Firm* — Polsinelli PC; Ron Galant (57) ABSTRACT

Provided are methods for prevention or treatment of an infection caused by a virus of *Flavivirus* genus, and in particular by Zika virus disease in a mammalian fetus. An example for such a treatment is a passive immunization of the fetus by an antibody, and in particular a polyclonal antibody or a fragment thereof.

21 Claims, 1 Drawing Sheet

THERAPY AND PROPHYLAXIS OF INFECTIOUS DISEASE CAUSED BY ZIKA VIRUS

FIELD OF THE INVENTION

The present invention relates to methods of treating a disease or disorder caused by a virus of the *Flavivirus* genus by using an active agent such as antiviral antibodies.

BACKGROUND OF THE INVENTION

Zika virus (ZIKV) is a member of the Flaviviridae virus family and the *Flavivirus* genus. In humans, it causes a disease known as Zika fever. It is related to dengue, yellow fever, West Nile and Japanese encephalitis, viruses that are also members of the virus family Flaviviridae. ZIKV is spread to people through mosquito bites. The most common symptoms of ZIKV disease (Zika) are fever, rash, joint pain, and red eye. The illness is usually mild with symptoms lasting from several days to a week. Today there is still no approved vaccine to prevent, or medicine to treat, Zika virus.

Travel tourism to nations where the recent epidemics were reported such as Polynesia has aided the geographical spread of the virus infection to Brazil, Columbia, Italy and to other countries. An autochthonous outbreak of the virus was reported in Italy caused by the locally established *Aedes* mosquitoes. In Asia, Zika virus infection has occurred sporadically in Cambodia, Thailand, Indonesia, Malaysia and Bangladesh although large epidemic outbreaks have not been reported in these regions. It seems the spread of the virus infection will keep extending to the U.S.A. and other regions in Europe and other locations.

The exact incidence of the rarer but potentially harmful viral infections during pregnancy, such as Zika virus and other flaviviridae is yet unknown, but may represent a clinically important problem due to the severity of the associated congenital abnormalities.

Zika virus can pass from a pregnant woman to her fetus during pregnancy or around the time of birth. Zika infection in pregnancy is a cause of microcephaly and other severe brain defects to the fetus. Other problems include eye defects, hearing loss, impaired growth, fetal loss, cognition disability and Guillain-Barré-Syndrom (GBS) Currently there are no active vaccines or other approved preventive medicine for Zika.

The current strategy, in case of maternal infection during the pregnancy, is to diagnose and treat the pregnant woman hoping that the woman will not pass the infection to the fetus. In case of fetal infection, pregnancy termination will be suggested.

SUMMARY OF THE INVENTION

Provided herein are methods and compositions for the treatment and/or prevention of a Zika viral infection. Also disclosed herein is a prophylactic treatment to protect a pregnant woman and her fetus against a Zika virus infection by using an enriched anti-Zika human immunoglobulin preparation provides passive immunity against Zika virus.

According to one aspect, provided herein is a method of treating a mammal infected with Zika virus comprising administering to the infected mammal a composition comprising human polyclonal antibodies or fragments thereof against the Zika virus. According to certain embodiments, said antibodies or the fragments thereof are IgG antibodies. According to certain embodiments, the treating is a passive immunization of a mammalian fetus. According to some embodiments, the fetus is a healthy fetus and said treatment is a prophylactic immunization. According to another embodiment, the fetus is infected by the Zika virus and the treatment is a passive immunization. According to some embodiments, said administering comprises single or multiple administrations. According to some embodiments, the treating comprises preventing or limiting one or more symptoms associated with infection by the virus. According to another embodiment, the composition is derived from a human serum that exhibits a neutralization titer of at least about 1:200 when evaluated according to a micro-neutralization test. According to some embodiments the neutralization titer is at least about 1:400. The composition demonstrated complete neutralization at a concentration of 92 mg/ml IgGs up to 1:5120 dilution, using the micro-neutralization method in Vero cells.

According to any one of the above embodiments, the administering comprises a route of administration selected from the group consisting of injection, inhalation, oral administration, and combinations thereof.

According to certain embodiments, said administering is performed by intravenous, intraarterial, subcutaneous, intramuscular, intraperitoneal, or intrathecal administration.

According to certain embodiments, said human polyclonal antibodies or fragments thereof are effective for treatment, or prophylaxis against different genotypic variants or strains of Zika virus. According to certain embodiments, the infected mammal is a pregnant woman or an immunocompromised subject. In certain embodiments, the treatment comprises administering the composition before a delivery to prevent contagion during the delivery.

According to certain embodiments, the method further prevents cross-reactions with a second species of Flaviviridae virus. According to certain embodiments, the method may reduce or prevent antibody-dependent enhancement (ADE) of disease associated with a second species of Flaviviridae virus.

According to certain embodiments, said Flaviviridae virus is dengue or yellow fever. According to certain embodiments, the method further comprises a second line treatment of an active vaccine against Zika virus.

According to certain embodiments, the antibodies are anti-Zika virus IgGs from one or more individuals previously infected with Zika virus. According to certain embodiments, said human polyclonal antibodies are purified or concentrated antibodies obtained from one or more methods selected from a. gel filtration, b. low conductivity precipitation, c. ion exchange column chromatography; and d. nanofiltration.

According to a certain aspect, provided herein is a pharmaceutical composition comprising an effective amount of human polyclonal antibodies or fragments thereof against Zika virus, and a pharmaceutically acceptable excipient. According to certain embodiments, the human polyclonal antibodies do not contribute to, cause, or induce Antibody Dependent Enhancement (ADE). In one embodiment, the human polyclonal antibodies do not contribute to, cause, or induce, antibody-dependent enhancement (ADE) of a Zika virus infection, or infection with one or more other viruses in the *Flavivirus* family, e.g. Dengue virus.

According to a certain aspect, provided herein is a method of neutralizing infectious Zika virus, the method comprising exposing a cell infected with Zika virus to a composition comprising one or more anti-Zika virus antibodies or fragments thereof described herein, wherein the exposing results in enhanced protection of the cell from virus infection, or from cell death.

According to a certain aspect, provided herein is a method of preventing, treating or ameliorating at least one symptom of a Zika virus infection, or of decreasing the frequency or severity of at least one symptom of a Zika virus infection, the method comprising administering a composition comprising the anti-Zika virus antibodies or fragments thereof described herein, to a subject in need thereof.

According to a certain aspect, provided herein is a method of decreasing the likelihood of transmitting Zika virus to a fetus of a pregnant female, and/or prevention of transmission to a reproductive organ of a male, the method comprising administering a pharmaceutical composition comprising at least one antibody or fragment thereof described herein to a subject in need thereof. In certain embodiments, the pharmaceutical composition is administered during the first trimester of pregnancy. In certain embodiments, the pharmaceutical composition is administered during the three trimesters of pregnancy.

According to a certain aspect, described herein is a method for treating or preventing placental Zika virus infection, comprising administering to a pregnant subject in need thereof, an effective amount of a pharmaceutical composition comprising at least one antibody or antibody fragment thereof described herein.

According to certain embodiments, the pregnant subject is infected with Zika virus or the pregnant subject is at risk of being infected with Zika virus.

According to a certain aspect, provided herein is a method of reducing fetal mortality in a pregnant subject, or reducing the risk of a pregnant subject giving birth to a child having microcephaly, comprising administering to the pregnant subject an effective amount of a pharmaceutical composition comprising at least one antibody described herein.

According to another aspect, provided herein is a pharmaceutical composition comprising an effective amount of an active compound, for use in treatment of a disease in a mammal fetus caused by a virus of the *Flavivirus* genus, wherein said active compound is capable of treating the disease and said pharmaceutical composition is administered intrauterinally. According to certain embodiments, said pharmaceutical composition is administered into the amniotic sac. According to certain embodiments, the active agent is an antibody. According to some embodiments, the virus is Zika virus and the antibodies are capable of biding to Zika virus. According to some embodiments, the fetus is a human fetus. According to one embodiment, the fetus is a healthy fetus and the treatment is a prophylactic immunization. According to another embodiment, the fetus is infected by a virus of *Flavivirus* genus such as Zika virus and the treatment is a passive immunization. According to any one of the above embodiments, the intrauterinal administration is selected from intra-amniotic administration, intraumbilical cord administration, intra-placental vasculature administration, intrafetus administration and administration by vaginal procedure.

According to a certain aspect, provided herein is a method of treating a disease or disorder caused by a virus of *Flavivirus* genus in a mammal fetus comprising administering intrauterinally a pharmaceutical composition comprising an effective amount of an active compound capable of treating the disease. According to some embodiments, the treatment is a prophylactic treatment. In certain embodiments, prophylactic treatment comprises administering the composition before a delivery to prevent contagion during the delivery. According to one embodiment, the delivery is vaginal delivery or via Cesarean section.

According to certain embodiments, the active compound is an anti-viral compound. According to certain exemplary embodiments, the active compound is an antibody. According to some embodiments, the antibody is a polyclonal antibody. According to some embodiments, the antibody is a monoclonal antibody.

The active compound may be administered to the amniotic sac, to the umbilical cord or directly to the fetus, e.g. intramuscularly. The administration may be single or multiple administration. According to some embodiments, the treatment or immunization is preventive, i.e. prophylactic treatment or immunization.

According to certain embodiments, provided herein is a method for passive immunization of a mammal fetus comprising administering intrauterinally a pharmaceutical composition comprising an effective amount of an antibody or fragment thereof, wherein the antibody or fragment thereof binds specifically to the pathogen. In some embodiments, the antibody or the fragment thereof is a non-maternal monoclonal antibody or a polyclonal antibody.

DETAILED DESCRIPTION OF THE INVENTION

According to some aspects, provided herein is a pharmaceutical composition comprising an effective amount of human polyclonal antibodies or fragments thereof against Zika virus for use in treatment or prophylaxis of infection in a mammal arising from Zika virus. The main target population of the pharmaceutical composition is pregnant women during an epidemic Zika outbreak, which may receive the treatment as a stand-alone drug for protection (one injection every 14 days, to cover the 1st trimester), or for protection within the first 14 days with future active vaccines.

Other target populations includes immuno-compromised populations (male and female) that can't receive an active vaccine, as well as last minute travelers (tourists, business travelers) to protect Zika exposed subjects at risk before the immune system is able to generate an effective therapeutic antibody level following active vaccine, or as a stand-alone treatment if such active vaccine is not available.

According to some aspects, provided herein is a pharmaceutical composition comprising an effective amount of an active compound, for use in treatment of a disease in a mammal fetus caused by a virus of the *Flavivirus* genus, wherein said active compound is capable of treating the disease.

The terms "treating" or "treatment" as used herein refers to taking steps to obtain beneficial or desired results, including clinical results. Beneficial or desired clinical results include, but are not limited to, alleviation or amelioration of one or more symptoms associated with an infectious disease, delay or slowing of that disease, amelioration, palliation or stabilization of that disease, and other beneficial results. According to some embodiments, the term "treating" has the meaning of "preventing". According to any one of the above embodiments, the treating or prevention of a disease is selected from inhibiting viral replication in a mammal embryo, inhibiting viral protein synthesis, preventing and/or inhibiting an increase in cell death in a mammal embryo and preventing and/or inhibiting an increase in fetus and later newborn death. The term "prophylactic treatment" refers to taking steps to prevent the disease, and in particular infectious disease. In one particular embodiment, prophylactic treatment comprises treatment before a delivery to prevent contagion during the delivery.

The term "effective amount" as used herein refers to a sufficient amount of the active compound that, when administered, will have the intended therapeutic effect.

The term "pharmaceutical composition" and "pharmaceutically acceptable composition" are used herein interchangeably and refer to a composition comprising the active compound as disclosed herein below, e.g. antibodies or fragment thereof, formulated together with one or more pharmaceutically acceptable carriers. Such composition may further comprise one or more active agents.

The term "fetus" and "embryo" are used herein interchangeable and refer to a multicellular diploid eukaryote during the embryogenesis, the prenatal development, pregnancy or gestation and during the delivery process, e.g. vaginal delivery or Cesarean section. This term refers to the developing organism during the whole process of prenatal development during the pregnancy and to the organism during the delivery such as vaginal delivery or Cesarean section. In one particular embodiment, the fetus is a human fetus. In human, the prenatal development is typically divided into three trimesters. Therefore in one embodiment, the term "fetus" refers to a fetus during the first, second and the third trimesters.

"Antibody-dependent-enhancement" or "ADE" is a mechanism by which a virus, when bound to antiviral antibodies that do not neutralize it, enters cells having Fc receptors, leading to increased infectivity in the cells. ADE can be observed in cells cultured in the laboratory, but rarely occurs in vivo. Most cases are known for infection with dengue virus, which is a member of the Flaviviridae family. This virus can use this mechanism to infect macrophages and other immune cells, causing a normally mild viral infection to become life-threatening.

The term "CCID50" refers to the quantity of virus infecting 50% of the cell culture. The CCID50 assay is a limit dilution assay with statistical titer calculation.

As used herein, a "Zika naive" subject refers to a subject who has not been infected by a Zika virus, i.e. a serum sample taken from said subject will produce a negative result in a Zika ELISA or Zika titer test.

As used herein, a "Zika immune" subject refers to a subject who has been infected by a Zika virus before administration of the composition described herein, i.e. a serum sample taken from said subject will produce a positive result in a Zika ELISA.

The term "Biological sample" refers to a sample obtained from a subject (such as a human or veterinary subject). Biological samples include, for example, fluid, cell and/or tissue samples. In some embodiments herein, the biological sample is a fluid sample. Fluid samples include, but are not limited to, serum, blood, plasma, urine, feces, saliva, cerebral spinal fluid (CSF) and bronchoalveolar lavage (BAL) fluid.

"Serum" means any fraction of blood serum that contains antibodies and one or more further protein blood components The term "purified," as used herein, is intended to refer to a composition, isolated from other components, wherein the protein is purified to any degree relative to its naturally-obtainable state. A purified protein therefore also refers to a protein, free from the environment in which it may naturally occur. Where the term "substantially purified" is used, this designation will refer to a composition in which the protein or peptide forms the major component of the composition, such as constituting about 50%, about 60%, about 70%, about 80%, about 90%, about 95% or more of the proteins in the composition.

As used herein an "effective dose" generally refers to that amount of the composition sufficient to induce immunity, to prevent and/or ameliorate virus infection or to reduce at least one symptom of infection and/or to enhance the efficacy of another dose of a composition. An effective dose may refer to the amount of the composition sufficient to delay or minimize the onset of an infection. An effective dose may also refer to the amount of the composition that provides a therapeutic benefit in the treatment or management of infection. Further, an effective dose is the amount with respect to the composition alone, or in combination with other therapies, that provides a therapeutic benefit in the treatment or management of a viral infection. An effective dose may also be the amount sufficient to enhance a subject's (e.g., a human's) own immune response against a subsequent exposure to virus.

"Neutralization titer" means quantification of an antibody that prevents or treats viral infection and subsequent detrimental viral effects, including cell death, in vitro, such as cell cultures including plaque assays, or in vivo, such as animal testing and clinical treatment. Antibodies that are shown present in a sample by ELISA, Western analyses, or like methods may or may not exhibit a neutralization titer.

"Affinity" as is known in the art, "affinity" is a measure of the tightness with a particular ligand (e.g., an antibody) binds to its partner (e.g., an epitope). Affinities can be measured in different ways.

The term "administering" includes any method of delivery of a pharmaceutical composition or agent (i.e., an immunological composition) into a subject's system or to a particular region in or on a subject. In certain embodiments of the invention, immunological compositions and/or antibodies are administered intramuscularly, subcutaneously, intradermally, intranasally, orally, subcutaneously, transcutaneously, or transmucosally to a subject. As used herein, and as based on context, the terms "administration" or "administrations" encompass a singular or multiple instances, respectively, of the delivery of an agent to a subject such that an immunogenically effective singular delivery as well as a priming delivery (first dose or administration) and a subsequent (second, third, etc., doses or administrations) boosting delivery of an agent(s) are encompassed.

According to some embodiments, said viral infection correlates with an increase in cell death in an animal or in a human infected by said virus. According to other embodiments, the infection and in particular viral infection is correlated with inhibiting fetus brain development.

The term "administering intrauterinely" and "intrauterine administration" are used herein interchangeably and refer to administration into any part of the uterus, administration within the interior of the uterus, and to any body located within the uterus such as placenta or fetus, such that the active compound reaches the fetus. According to one embodiment, the intrauterine administration is invasive. Examples of such administration is administration during amniocentesis, amniotic sac puncture and/or injection and injection into the placental vasculature or umbilical cord, e.g. into umbilical vein. The administration encompasses also administration into the fetal side of the maternal-fetal interface. Direct administration to the fetus is encompassed as well.

The term "amniocentesis" as used herein refers to a medical procedure during which the amniotic sac is punctured. During the procedure amniotic fluid may be taken for diagnostic purposes. Therefore in one embodiment, the administration of an active agent is performed during the amniocentesis procedure in which amniotic fluid is taken.

The administration, and in particular amniocentesis may be performed with or without a guidance. Examples for the guidance are optical, ultrasound and injection guides.

According to some embodiments, the virus of the *Flavivirus* genus is selected from Zika virus, Yellow fever virus, Dengue fever virus, Japanese encephalitis virus, West Nile encephalitis virus, virus causing to Kyasanur Forest, Murray Valley encephalitis virus, St. Louis encephalitis virus, Usutu encephalitis virus, Tick-borne encephalitis virus, and Omsk hemorrhagic fever virus.

According to some embodiments, said viral infection correlates with an increase in cell death in an animal or in a human infected by said virus. According to other embodiments, the infection and in particular viral infection is correlated with inhibiting fetus brain development.

Zika Virus

Along with other viruses in the Flaviviridae family, Zika virus is enveloped and icosahedral with a non-segmented, single-stranded, positive sense RNA genome. It is most closely related to the Spondweni virus and is one of the two viruses in the Spondweni virus Glade. The virus was first isolated in 1947 from a rhesus monkey in the Zika Forest of Uganda, Africa and was isolated for the first time from humans in 1968 in Nigeria. From 1951 through 1981, evidence of human infection was reported from other African countries such as Uganda, Tanzania, Egypt, Central African Republic, Sierra Leone and Gabon, as well as in parts of Asia including India, Malaysia, the Philippines, Thailand, Vietnam and Indonesia. It is transmitted by mosquitoes and has been isolated from a number of species in the genus *Aedes-Aedes aegypti, Aedes africanus, Aedes apicoargenteus, Aedes furcifer, Aedes luteocephalus* and *Aedes vitattus*. Studies show that the extrinsic incubation period in mosquitoes is about 10 days. The vertebrate hosts of the virus include monkeys and humans. As of early 2016, the most widespread outbreak of Zika fever, caused by the Zika virus, is ongoing primarily in the Americas. The outbreak began in April 2015 in Brazil, and subsequently spread to other countries in South America, Central America, and the Caribbean.

The Zika virus was first linked with newborn microcephaly during the Brazil Zika virus outbreak. In 2015, there were 2,782 cases of microcephaly compared with 147 in 2014 and 167 in 2013. The Brazilian Health Ministry has reported 4783 cases of suspected microcephaly as of January 30, an increase of more than 1000 cases from a week earlier. Confirmation of many of the recent cases is pending, and it is difficult to estimate how many cases went unreported before the recent awareness of the risk of virus infections. What is important is not only the number of cases but also the clinical manifestation of the cases. Brazil is seeing severe cases of microcephaly, which are more likely to be paired with greater developmental delays. Most of what is being reported out of Brazil is microcephaly with other associated abnormalities. The potential consequence of this is the fact that there are likely to be subclinical cases where the neurological sequelae will only become evident as the children grow. Zika virus has also been associated with an increase in a rare condition known as Guillain-Barre, where the infected individual becomes essentially paralyzed. During the Zika virus outbreak in French Polynesia, 74 patients which had had Zika symptoms-out of them, 42 were diagnosed as Guillain-Barre syndrome. In Brazil, 121 cases of neurological manifestations and Guillain-Barre syndrome (GBS) were reported, all cases with a history of Zika-like symptoms.

The terms "active agent" and "active moiety" are used herein interchangeable and refer to any molecule, drug, compound, composition of matter or mixture thereof which provides the desired pharmacologic effects, e.g. treating the disease caused by a virus of *Flavivirus* genus. According to some embodiments, the active agent is an antibody or fragment thereof capable of treating the disease. According to another embodiment, the active agent is a small molecule capable of treating the disease.

According to any one of the above embodiments, the active agent is an antibody or fragment thereof that binds specifically to the virus of *Flavivirus* genus. According to one embodiment, the treatment comprises a passive immunization of the mammal fetus. Thus, according to one embodiment, provided herein is a pharmaceutical composition comprising an effective amount of antibodies which bind specifically to a virus of *Flavivirus* genus, for use in passive immunization of a mammal fetus.

The terms "passive immunization" and "passive vaccination" are used herein interchangeably and refer to a process of providing or administering an exogenous antibody or a fragment thereof to an organism in order to treat an infectious disease caused by a pathogen or to prevent a contagion by that pathogen.

The term "exogenous antibody" refers to an antibody or a fragment thereof that is not originated from the fetus. Exogenous antibody may be of maternal origin or of non-maternal origin. Thus according to one embodiment, the antibody is an exogenous antibody.

According to some embodiments, the antibody is a non-maternal antibody or a fragment thereof. Therefore, according to some embodiments, the treatment encompasses non-maternal immunization of a fetus.

The term "non-maternal immunization" refers to immunization by an antibody or a fragment thereof that is not originated from the mother. Therefore, in one embodiment, the treatment comprises administering an antibody or fragment thereof with a proviso that said antibody is a non-maternal antibody, i.e. is not originated from the mother.

According to some embodiments, the antibody is a polyclonal antibody or a fragment thereof. According to a further embodiment, the antibody is a non-maternal polyclonal antibody or a fragment thereof. According to some embodiments, the antibody is a monoclonal antibody or a fragment thereof. According to a further embodiment, the antibody is a non-maternal monoclonal antibody or a fragment thereof.

The term "antibody" and "antibodies" are used here interchangeably in its broadest sense and includes monoclonal antibodies (including full length or intact monoclonal antibodies), polyclonal antibodies, multivalent antibodies, multi-specific antibodies (e.g., bi-specific antibodies), and antibody fragments long enough to exhibit the desired biological activity.

An antibody is a molecule comprising at least the antigen-binding portion of an antibody. Antibody or antibodies according to the invention include intact antibodies, i.e. monoclonal antibodies (mAbs), as well as proteolytic fragments thereof, such as the Fab or F(ab')$_2$ fragments. Single chain antibodies also fall within the scope of the antibodies described herein.

Antibodies, or immunoglobulins, comprise two heavy chains linked together by disulfide bonds and two light chains, each light chain being linked to a respective heavy chain by disulfide bonds in a "Y" shaped configuration. Proteolytic digestion of an antibody yields Fv (Fragment variable) and Fc (Fragment crystalline) domains. The antigen binding domains, Fab, include regions where the polypeptide sequence varies. The term F (ab')$_2$ represents two Fab' arms linked together by disulfide bonds. The central axis of the antibody is termed the Fc fragment. Each heavy chain has at one end a variable domain ($V_H$) followed by a number of constant domains ($C_H$). Each light chain has a variable domain ($V_L$) at one end and a constant domain ($C_L$) at its other end, the light chain variable domain being aligned with the variable domain of the heavy chain and the light chain constant domain being aligned with the first constant domain of the heavy chain (CH1). The variable domains of each pair of light and heavy chains form the antigen-binding site. The domains on the light and heavy chains have the same general structure and each domain comprises four framework regions, whose sequences are relatively conserved, joined by three hyper-variable domains known as complementarity determining regions (CDRs 1-3). These domains contribute specificity and affinity of the antigen-binding site. The isotype of the heavy chain (gamma, alpha, delta, epsilon or mu) determines immunoglobulin class (IgG, IgA, IgD, IgE or IgM, respectively). The light chain is either of two isotypes (kappa, κ or lambda, λ) found in all antibody classes.

The term "polyclonal antibody" denotes a mixture of different antibody molecules which react with more than one immunogenic determinant of an antigen. In the present context, the term "polyclonal antibody" encompasses a polyclonal antibody isolated or purified from mammalian blood, secretions, or other fluids, or from eggs, as well as a mixture of different monoclonal antibodies, and finally a polyclonal antibody may be produced as a recombinant polyclonal antibody.

The term "monoclonal antibody" (mAb) as used herein refers to an antibody obtained from a population of substantially homogeneous antibodies, i.e., the individual antibodies comprising the population are identical except for possible naturally occurring mutations that may be present in minor amounts.

Monoclonal antibodies (mAbs) are highly specific, being directed against a single antigen. Furthermore, in contrast to polyclonal antibody preparations that typically include different antibodies directed against different determinants (epitopes), each monoclonal antibody is directed against a single determinant on the antigen. The modifier "monoclonal" is not to be construed as requiring production of the antibody by any particular method. mAbs may be obtained by methods known to those skilled in the art. For example, the monoclonal antibodies may be made by the hybridoma method first described by Kohler et al., Nature 1975, 256, 495, or may be made by recombinant DNA methods (see, e.g., U.S. Pat. No. 4,816,567). The "monoclonal antibodies" may also be isolated from phage antibody libraries using the techniques described in Clackson et al., Nature 1991, 352, 624-628 or Marks et al., J. Mol. Biol., 1991, 222:581-597, for example.

The mAbs may be of any immunoglobulin class including IgG, IgM, IgE, IgA. A hybridoma producing a mAb may be cultivated in-vitro or in-vivo. High titers of mAbs can be obtained by in-vivo production where cells from the individual hybridomas are injected intra-peritoneally into pristine-primed Balb/c mice to produce ascites fluid containing high concentrations of the desired mAbs. mAbs of isotype IgM or IgG may be purified from such ascites fluids, or from culture supernatants, using column chromatography methods well known to those of skill in the art.

Also provided herein are conservative amino acid variants of the antibody molecules described herein. Variants may also be made that conserve the overall molecular structure of the encoded proteins. Given the properties of the individual amino acids comprising the disclosed protein products, some rational substitutions will be recognized by the skilled worker. Amino acid substitutions, i.e. "conservative substitutions" may be made, for instance, on the basis of similarity in polarity, charge, solubility, hydrophobicity, hydrophilicity, and/or the amphipathic nature of the residues involved. The term "antibody analog" as used herein refers to an antibody derived from another antibody by one or more conservative amino acid substitutions.

The term "antibody variant" as used herein refers to any molecule comprising the antibody. For example, fusion proteins in which the antibody or an antigen-binding-fragment thereof is linked to another chemical entity is considered an antibody variant "Antibody fragments" comprise only a portion of an intact antibody, generally including an antigen binding site of the intact antibody and thus retaining the ability to bind antigen. Examples of antibody fragments encompassed by the present definition include: (i) the Fab fragment, having VL, CL, VH and CH1 domains; (ii) the Fab' fragment, which is a Fab fragment having one or more cysteine residues at the C-terminus of the CH1 domain; (iii) the Fd fragment having VH and CH1 domains; (iv) the Fd' fragment having VH and CHI domains and one or more cysteine residues at the C-terminus of the CH1 domain; (v) the Fv fragment having the VL and VH domains of a single arm of an antibody; (vi) the dAb fragment (Ward et al., Nature 1989, 341, 544-546) which consists of a VH domain; (vii) isolated CDR regions; (viii) F(ab')$_2$ fragments, a bivalent fragment including two Fab' fragments linked by a disulphide bridge at the hinge region; (ix) single chain antibody molecules (e.g. single chain Fv; scFv) (Bird et al., Science 1988, 242, 423-426; and Huston et al., PNAS (USA) 1988, 85, 5879-5883); (x) "diabodies" with two antigen binding sites, comprising a heavy chain variable domain (VH) connected to a light chain variable domain (VL) in the same polypeptide chain (see, e.g., EP 404,097; WO 93/11161; and Hollinger et al., Proc. Natl. Acad. Sci. USA, 1993, 90, 6444-6448); (xi) "linear antibodies" comprising a pair of tandem Fd segments (VH-CH1-VH-CH1) which, together with complementary light chain polypeptides, form a pair of antigen binding regions (Zapata et al. Protein Eng., 1995, 8, 1057-1062; and U.S. Pat. No. 5,641,870).

Single chain antibodies can be single chain composite polypeptides having antigen binding capabilities and comprising amino acid sequences homologous or analogous to the variable regions of an immunoglobulin light and heavy chain i.e. linked $V_H$-$V_L$ or single chain Fv (scFv).

According to some embodiments, the polyclonal antibody or the antibody fragment is selected from a non-human mammalian antibody and a human antibody.

According to some embodiments, the monoclonal antibody or the antibody fragment is selected from the group consisting of a non-human mammalian, human, humanized and chimeric antibody, and an antibody fragment of the foregoing.

The term "human antibody" as used herein refers to an antibody which possesses an amino acid sequence which corresponds to that of an antibody produced by a human and/or has been made using any of the techniques for making human antibodies as disclosed herein. This definition of a human antibody specifically excludes a humanized antibody comprising non-human antigen-binding residues. Human antibodies can be produced using various techniques known in the art.

The term "humanized antibody" as used herein refers to an antibody that has its CDRs (complementarily determining regions) derived from a non-human species immunoglobulin and the remainder of the antibody molecule derived mainly from a human immunoglobulin.

As used herein, the term "chimeric antibody" refers to an antibody in which at least one of the antibody chains (heavy or light) comprises variable region sequences from one species (e.g., mouse) and constant region sequences from another species (e.g., human). The term "chimeric antibody" is intended to encompass antibodies in which: (i) the heavy chain is chimeric but the light chain comprises variable and constant regions from only one species; (ii) the light chain is chimeric but the heavy chain comprises variable and constant regions from only one species; and (iii) both the heavy chain and the light chain are chimeric.

According to some embodiments, the monoclonal antibody or the antibody fragment may be of non-human mammal origin. Examples of such antibodies are mouse, rat, rabbit, goat, mouse, rat, rabbit, goat, ape, and monkey antibodies. In one particular embodiment, the antibody or the antibody fragment is a mouse antibody or antibody fragment.

The polyclonal antibody or the monoclonal antibody or the antibody fragment according to any one of the above embodiments has an IgG, IgA, IgD, IgE or IgM structure. In one particular embodiment, the antibody or the antibody fragment, e.g. monoclonal antibody or the antibody fragment has an IgG structure.

According to some embodiments, the antibody or the fragment thereof, and in particular a polyclonal antibody or a fragment thereof is specific to Zika virus. According to another embodiment, the antibody or the fragment thereof is specific to Dengue virus. According to another embodiment, the antibody or the fragment is selected from the antibody or the fragment specific to a virus selected from Yellow fever virus, Japanese encephalitis virus, West Nile encephalitis virus, Usutu encephalitis virus, and Bagaza encephalitis virus. According to such embodiments, the antibodies are human or humanized antibodies. According to a further embodiment, the antibodies are IgG antibodies. According to any one of the above embodiments, the treatment is a passive immunization of the mammal fetus.

According to some embodiments, the fetus is a fetus infected by a virus of *Flavivirus* genus. According to one embodiment, the fetus is infected by Zika virus. According to other embodiments, the fetus is infected by a virus causing a disease selected from Yellow fever, Dengue fever, Japanese encephalitis, West Nile encephalitis, Kyasanur Forest disease, Murray Valley encephalitis, St. Louis encephalitis, Tick-borne encephalitis, and Omsk hemorrhagic fever.

According to some embodiments, said viral infection correlates with an increase in cell death in an animal or in a human infected by said virus. According to other embodiments, the infection and in particular viral infection is correlated with inhibiting fetus brain development.

According to some embodiments, the fetus is a healthy fetus. Thus, according to one embodiment, the treatment is prophylactic or preventive treatment. According to a further embodiment, the treatment is a prophylactic immunization.

According to any one of the above embodiments, the mammal fetus is a human or non-human fetus. According to one embodiment, the fetus is a human fetus. According to another embodiment, the fetus is a non-human mammal fetus. The non-human fetus may be a fetus of a livestock animal such as a cattle, pig, sheep, goat, horse, mule, ass, buffalo, or camel. In one particular embodiment, the fetus is cattle fetus. In some other embodiment, the domestic pet fetus is a cat or dog fetus; the rodent fetus is a fetus of a mouse, rat, guinea pig or hamster; the lagomorpha fetus is a rabbit fetus; and the primate fetus is monkey such as a macaque, or an ape fetus such as a chimpanzee.

According to any one of the above embodiments, the pharmaceutical composition further comprises one or more pharmaceutically acceptable excipients.

The terms "pharmaceutically acceptable carrier" or "pharmaceutically acceptable excipient" as used herein refer to any and all solvents, dispersion media, preservatives, antioxidants, coatings, isotonic and absorption delaying agents, surfactants, buffer and the like, that are compatible with pharmaceutical administration. The use of such media and agents for pharmaceutically active substances is well known in the art. The compositions may contain other active compounds providing supplemental, additional, or enhanced therapeutic functions.

According to one embodiment, the pharmaceutical composition is formulated as an extended release formulation.

The term "extended release", "controlled release" or "sustained release," as used herein interchangeably, refers to a mode of releasing an active agent from the formulation such that it is available to an organism over a period of time. An extended release formulation of an active agent may be accomplished, e.g., by embedding the active agent in a web of substance that dissolves slowly, such that the active ingredient slowly and regularly leeches from the coating, or by swelling up the active agent to form a gel with a nearly impenetrable surface, wherein the drug slowly exits the semipermeable layer.

According to some embodiments, provided herein is a pharmaceutical composition comprising an effective amount of non-maternal antibodies or fragments thereof, which may be used to treat a human fetus, wherein said antibodies or fragments thereof are capable of binding to a virus of the *Flavivirus* genus. According to one embodiment, the virus is selected from Zika virus, Dengue virus, Yellow fever virus, Japanese encephalitis virus, West Nile encephalitis virus, Usutu encephalitis virus, and Bagaza encephalitis virus. According to some embodiments, the antibodies or fragments thereof are human, humanized or chimeric antibodies. According to one embodiment, the fetus is a healthy fetus. According to another embodiment, the fetus is infected by Zika virus. According to one embodiment, the antibodies are polyclonal antibodies.

According to some embodiments, provided herein is a pharmaceutical composition comprising an effective amount of non-maternal antibodies or fragments thereof, which may be used to treat a human fetus, wherein said antibodies or fragments thereof are capable of binding to Zika virus. According to one embodiment, the antibodies are polyclonal antibodies. According to other embodiments, the antibodies or fragments thereof are human, humanized or chimeric antibodies. According to one embodiment, the fetus is a healthy fetus. According to another embodiment, the fetus is infected by Zika virus.

According to some embodiments, provided herein is a pharmaceutical composition comprising an effective amount of non-maternal antibodies or fragments thereof, which may be used to treat a healthy human fetus, wherein said antibodies or fragments thereof are selected from polyclonal antibodies, and monoclonal antibodies selected from humanized, chimeric and human antibodies, and fragments of the foregoing capable of binding to a Zika virus.

According to another aspect, provided herein is a method for treating a disease caused by a virus of the *Flavivirus* genus in a mammalian fetus comprising administering a pharmaceutical composition comprising an effective amount of an active compound capable of treating the disease. According to some embodiments, the virus is selected from the group consisting of Zika virus, Dengue virus, Yellow fever virus, Japanese encephalitis virus, West Nile encephalitis virus, Usutu encephalitis virus, and Bagaza encephalitis virus.

According to some embodiments, the active agent is an antibody or fragment thereof that binds specifically to the virus of *Flavivirus* genus. According to some embodiments, the antibody is a non-maternal antibody or a fragment thereof. According to a further embodiment, the antibody is a polyclonal antibody or a fragment thereof. According to one embodiment, the antibody or a fragment thereof is human. According to a further embodiment, the antibody is a monoclonal antibody or a fragment thereof.

According to some embodiments, the antibody or the fragment thereof, and in particular a polyclonal antibody or a fragment thereof is specific to Zika virus. According to another embodiment, the antibody or the fragment thereof is specific to Dengue virus. According to another embodiment, the antibody or the fragment is specific to a virus selected from Yellow fever virus, Japanese encephalitis virus, West Nile encephalitis virus, Usutu encephalitis virus, and Bagaza encephalitis virus. According to a further embodiment, the antibodies are IgG antibodies. According to any one of the above embodiments, the treatment is a passive immunization of the mammal fetus.

According to some embodiments, the fetus is a human fetus. According to other embodiment, the fetus is non-human mammal fetus. According to some embodiments, the fetus is a healthy fetus and the treatment is a prophylactic immunization. According to another embodiment, the fetus is infected by a virus of *Flavivirus* genus, and in particular infected by Zika virus.

In any one of the above embodiments, the term "consisting of" may be substituted for the term "comprising."

Having now generally described the invention, the same will be more readily understood through reference to the following examples, which are provided by way of illustration and are not intended to be limiting of the present invention.

EXAMPLES

Example 1. Anti-ZIKV IgG Purified from Plasma of Convalescent Donors Methods

Anti-ZIKV IgGs were purified from the plasma of seven convalescent donors that are ZIKV-free and had high titer of Anti-ZIKV antibodies (50% neutralization at dilution ≥1:80). IgGs purification was conducted using protein-G (Protein G Sepharose®, ab193259, abcam). The titer of the IgGs pool was determined by a serial dilution of the antibodies in a neutralization assay using K-562 cells that were infected by ZIKA virus, in a 96-wells plate.

Antibodies-dependent enhancement (ADE) assays were performed according to Paul L M et al. 2016 (*Clin Transl Immunology*. Dec. 16; 5(12)). ADE was tested by neutralization assay and determination of viral RNAs that accumulate in the K-562 cells in the presence of serum from Dengue-naive donors serum as a control, and serum from Dengue convalescent donors.

One TCID50 of Zika virus (ZIKV) MR766 (as determined using Vero cells) was mixed with human sera (Control or DENY positive) and 100 µl PRMI medium (for 'no antibody' control). Purified ZIKV antibodies or CTRL non-specific antibodies were used in a 100 µl volume and incubated for 1 h at 37° C. Mixtures were added to 80,000 K562 cells in 150 µl of complete RPMI medium and incubated for three days at 37° C., 5% (v/v) $CO_2$. Cells were then collected and total RNA was isolated using NucliSENS easyMAG system (bioMérieux, Marcy l'Etoile, France) according to the manufacturer's instructions. qRT-PCR with specific primers and probes set for the ENV protein gene was used as previously described (Lanciotti R S, Kosoy O L, Laven J J, Velez J O, Lambert A J, Johnson A J, et al. Genetic and serologic properties of Zika virus associated with an epidemic, Yap State, Micronesia, 2007. Emerg Infect Dis. 2008; 14(8):1232-9. DOI: 10.3201/eid1408.080287 PMID: 18680646), to detect ZIKV RNA presence.

Results

Titration of ZIKV purified antibody sample was 1:5120 in a micro-neutralization assay. A cell-culture based ADE assay (using K562 cells), was established and showed enhanced ZIKV infection in the presence of anti-Dengue serum compare to naïve serum. Dilution of the serum resulted in a lower infection rate, demonstrating that the infection was dependent on the levels of anti-Dengue antibodies.

Figure 1:
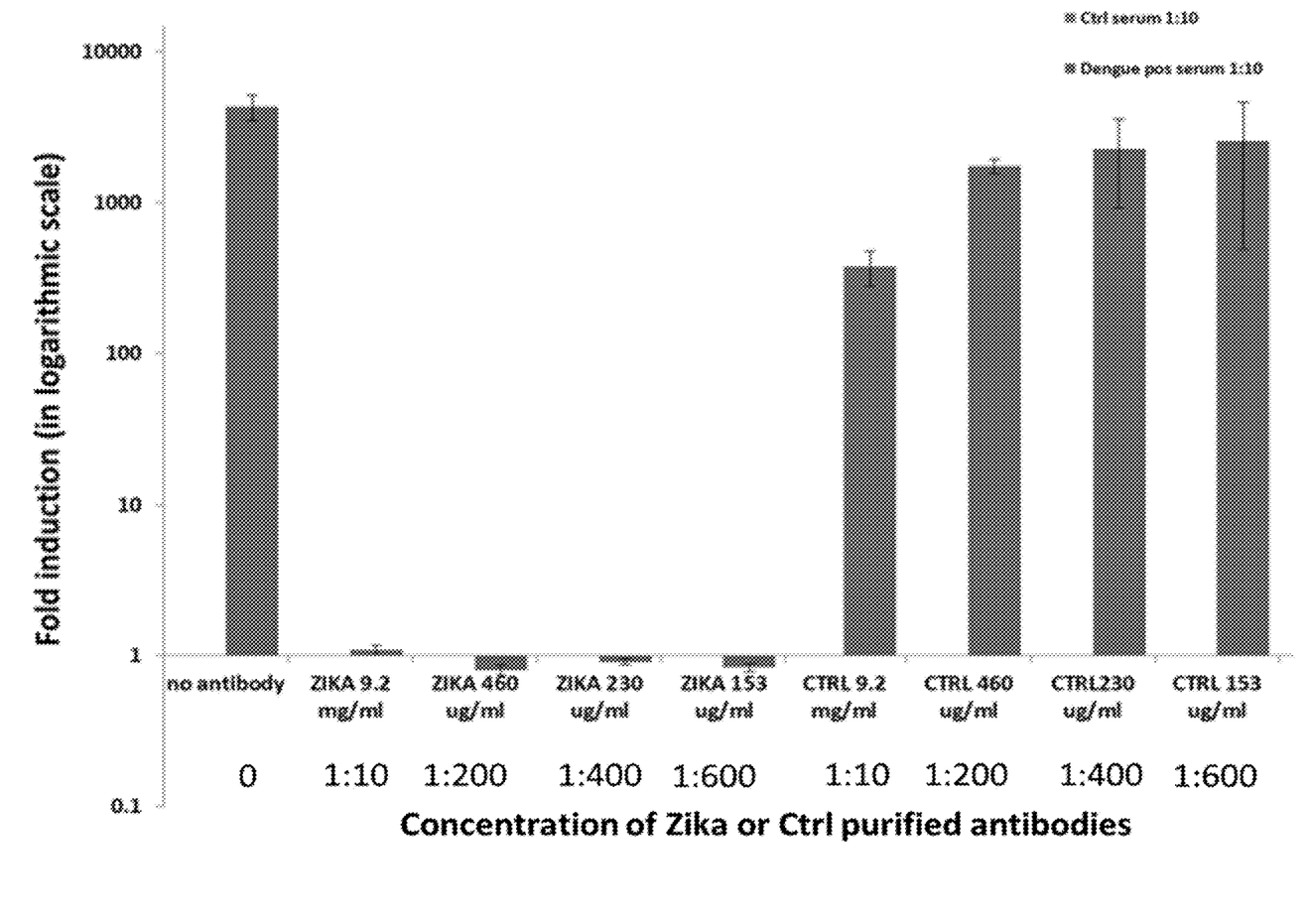
FIG. 1 shows the results of an assay for measuring antibody dependent enhancement (ADE) using anti-Zika virus antibodies described herein.

FIG. 1 demonstrates the results of ADE assays in the presence of the anti-Zika virus antibodies described herein. The Anti-Zika IgGs at a concentration of 92 mg/ml demonstrated complete neutralization of ZIKV up to 1:5120 dilution. Anti-Zika IgGs neutralize ZIKV and prevent ADE up to 1:600 dilution according to the K562 ADE cell assay.

The demonstration of ADE prevention due to the established neutralizing effect of anti-ZIKA IgGs on ZIKV indicates that prophylactic treatment with an enriched anti-Zika human immunoglobulin preparation can provide passive immunity against the Zika virus, without a risk of ADE.

Example 2. Anti-Zika Hyperimmune IgG Laboratory Scale Batch and Uses Thereof for Studies in a Mouse Model Study Goals and Objectives The study aims to produce human plasma-derived Anti-Zika IgG for injection to ZikV-infected pregnant mice and to evaluate the safety and efficacy of anti-Zika antibodies in terms of protection of the mother and the fetuses. The study aims to provide a medical countermeasure against maternal-fetal transmission, infection and disease caused by the Zika virus. The plasma-derived IgGs are superior to mAbs due to the broader spectrum of epitopes that are targeted by polyclonal IgGs from plasma pools of heterogeneous human donors. The plasma-derived IgG is the best solution as a preventative of abnormal brain development in newborns and fetus of a post-exposure pregnant woman.

Methodology

Production of Anti-ZIKA Hyperimmune IgG Laboratory Scale Batch

Plasma units from convalescent donors are pooled and IgGs are purified using Protein G chromatography to obtain a hyperimmune-IgGs laboratory scale batch. The plasma pool titer is determined using a quantitative Cellular assay (Plaque Reduction Neutralization Test, PRNT). Plasma is aliquoted, and kept frozen for use and establishment of the therapeutic dose.

Preclinical Studies for Prove of Concept and Dose Determination

The Ifnar 1 −/− (or A129) Mouse Model

Two mouse models of Zika disease were recently characterized which are susceptible to lethal and nonlethal Zika virus infection. The models are immunocompromised mice lacking the receptor for type I interferon (IFN $\alpha/\beta$) on a C57BL/6 background (Ifnar1 −/− mice, Lazear et al., 2016, Cell Host & Microbe, May 11; 19(5):720-30), or on 129 background (A129, Sapparapu et al., 2016, Nature. Dec. 15; 540(7633):443-447). Ifnar1 −/− mouse strains (alternatively A129 mice) are used to determine the therapeutic dose that will protect from the ZIKV effect.

Human Anti-Zika IgG Lethal Protection Dose Determination

Young Ifnar1 −/− mice (4 week old) are used to determine the Anti-Zika IgG dose that is effective in preventing weight loss, neurological disease, high viral load in the brain, spinal cord and testes, and/or death.

Three groups of eight young mice each are infected with $1\times10^3$ PFU/mouse by the subcutaneous route (SC) in the footpad. An additional mock infected control group of 4 mice are given PBS by the same route. At day 1 post infection (PI), Anti-Zika IgGs are administered at low and high doses (Groups A and B, respectively) via an intraperitoneal or IV route. Additional group is injected with non-specific antibodies, as control. Mice are monitored three times each day for clinical signs of disease as described in Table 1.

TABLE 1

Numerical scoring of mice:

| Scoring | Clinical observation |
|---|---|
| 0 | Normal |
| 2 | ruffled fur |
| 3 | lethargy, pinched, hunched, wasp waisted |
| 5 | labored breathing, rapid breathing, inactive, neurological |
| 10 | Immobile |

Weights are recorded daily. These mice should begin to lose weight at day 5 post infection (PI), at day 7 PI they lose between 15-25% of their starting weight. Hindlimb weakness is observed in most at d6 PI, and partial to complete paralysis at d7 PI. A set of humane clinical end points are a 20% weight loss, or 10% weight loss and a clinical symptom, which mandated euthanasia, as are determined by the veterinary stuff.

At Day 7 post-challenge, mice are sacrificed, and a group of four animals from each group are undergoing necropsy. Samples of spleen, liver, brain and ovary are collected and immediately frozen at −80° C. for virological analysis or kept in tubes containing 10% neutral buffered saline for microscopic analysis. Blood is collected into RNAprotect tubes (Qiagen, UK) for viral load testing.

Anti-Zika IgG-Pregnant Mouse Protection Experiment

Ifnar 1 −/− (or A129) pregnant mice are infected with ZIKV pre or post treatment with Anti-Zika IgG, and newborns are evaluated immediately after birth (as described by Sapparapu et al., 2016, Nature. Dec. 15; 540(7633):443-447).

Prophylactic Study:

Two groups of 10 Ifnar 1 −/− female mice each (groups A and B), and a control group (C) of 5 Ifnar 1 −/− female mice, are mated with WT B57BL/6 males. Pregnant females (estimated 8/group) continued in the study. At embryonic day E5.5 pregnant mice in group A are treated with the therapeutic dose of Anti-Zika IgG (that was determined in the previous study). Pregnant mice in group B are treated with non-specific antibodies as a control. At E6.5 all mice are infected with $1\times10^3$ PFU/mouse by SC injection in the footpad. An additional mock infected mice control group (group C) is given PBS by the same route.

Therapy Study:

As above, where at E5.5 pregnant mice in group A and B are infected with $1\times10^3$ PFU/mouse by SC injection in the footpad, while group C are given PBS. At E6.5, mice are treated with the therapeutic dose of Anti-Zika IgG.

Treatment includes administration of Anti-Zika IgG by Intra-mascular (IM) or IV administration and newborns are evaluated immediately after birth for intrauterine growth restriction, ZIKV infection and injury of the fetal brain.

Example 3. Uses of Anti-Zika Hyperimmune IgG for Preclinical Studies in a Pig Model Pregnant pigs are infected with ZIKV post treatment with Anti-Zika IgG, and newborns are evaluated immediately after birth (newborns size, ZIKA infection and damage to the brain).

1. Before the animal trial begins, the IgG product will be tested for viral neutralization effects in vitro at VIDO-InterVac to ensure that it neutralizes the ZIKV virus strain [Asian-lineage ZIKV strain PRVABC59 (GenBank: KU501215) isolated from human serum collected in Puerto Rico in December 2015] that is used in the animal study to determine the product's titer.

2. Two pregnant sows will be used in the study, one for Anti-ZIKV polyclonal antibodies (Ab) treatment (Sow #1) and the other for isotype-matched non-specific Ab treatment (Sow #2). Sows will be purchased from the Prairie Swine Centre (Saskatoon Canada) and will be transported to VIDO-InterVac animal facility and acclimatized for 5 to 10 days.

3. At 50 days gestation, laparotomy of sow and trans-uterus injection of treatment into the amniotic sac (0.1 ml), peritoneal cavity (0.1 ml) and intra-allantoic (0.1 ml) of the $3^{rd}$ and $5^{th}$ fetuses, followed by injection of $10^4$ $TCID_{50}$ into the amniotic sac (0.1 ml) and peritoneal cavity (0.1 ml) of the first and second fetuses after 15 minutes, i.e.: TIP OF HORN: Fetus 1 (ZIKV)—Fetus 2 (ZIKV)—Fetus 3 (TREATED)—Fetus 4 (non-treated)—Fetus 5 (TREATED)—Fetus 6 (non-treated). The remaining fetuses (about 6) will not be tested. The treatment materials will be provided in a ready-for-use format.

4. Animals are observed at least once per day during the course of the study. Following challenge all gilts are observed at least twice daily and any deviations from normal behavior are recorded.

5. Sows/fetuses (total of 6 per sow) will be sacrificed 14 days after infection/treatment. Tissue samples of fetuses will be collected for examinations. At necropsy, the weights of each of the 24 fetuses and each fetal brain will be measured.

5.1 Brain tissue for qRT-PCR of Zika virus: two separate pieces per fetus for the 6 fetuses per sow, i.e. cerebrum cortex and cerebellum cortex. (2×6 fetuses×2 sows=24 samples).

5.2 Amniotic fluids of the 6 fetuses per sow for determination of TCID50 of Zika virus. (12 samples).

5.3 Tissues will be collected from fetuses (up to 12 fetuses per sow including the 6 fetuses), freeze/store for 6 months for future use:

a. Placenta (24), amniotic membrane (24) and amniotic fluid (12) or left-over amniotic fluid samples (12).

b. Brain (12) or the remaining brain tissues (12).

6. Potential outcomes: if the antibodies work, they should prevent Zika virus transmission from infected fetuses to adjacent Ab-treated fetuses in Sow #1. In the control Sow #2, the adjacent fetuses will be infected with Zika virus via trans-fetal infection.

Although the present invention has been described herein above by way of preferred embodiments thereof, it can be modified, without departing from the spirit and nature of the subject invention as defined in the appended claims

The invention claimed is:

1. A method of treating a mammal in need of treatment for a Zika virus infection, the method comprising administering to the infected mammal a composition comprising human polyclonal antibodies or fragments thereof against the Zika virus wherein the human polyclonal antibodies are purified from a human serum or plasma.

2. The method of claim 1, wherein said antibodies or fragments thereof are IgG antibodies.

3. The method of claim 1, wherein said treating is-results in a passive immunization of a mammalian fetus.

4. The method of claim 3, wherein said fetus is a healthy fetus and said treatment is a prophylactic immunization.

5. The method of claim 1, wherein said administering comprises single or multiple administrations.

6. The method of claim 1, wherein said treating comprises preventing or limiting one or more symptoms associated with infection by the virus.

7. The method of claim 1, wherein the human polyclonal antibodies are purified from a human serum, and wherein the human polyclonal antibodies exhibit a neutralization titer of at least about 1:200 when evaluated according to a microneutralization test.

8. The method of claim 1, wherein said administering comprises a route of administration selected from the group consisting of injection, inhalation, oral administration, and combinations thereof.

9. The method of claim 1, wherein said administering is performed by intravenous, intraarterial, subcutaneous, intramuscular, intraperitoneal, intrauterinal, or intrathecal administration.

10. The method of claim 1, wherein said human polyclonal antibodies or fragments thereof are effective for treatment or prophylaxis against different genotypic variants or strains of Zika virus.

11. The method of claim 1, wherein the infected mammal is a pregnant woman or an immunocompromised subject.

12. The method of claim 1, wherein the method further prevents antibody-dependent enhancement (ADE) of a disease associated with a second species of Flaviviridae virus.

13. The method of claim 12, wherein said second species of Flaviviridae virus is dengue or yellow fever.

14. The method of claim 1, wherein the method further comprises administering to the infected mammal a second line treatment of an active vaccine against Zika virus.

15. The method of claim 1, wherein the antibodies are anti-Zika virus IgG from one or more individuals previously infected with Zika virus.

16. The method of claim 1, wherein said human polyclonal antibodies are purified or concentrated antibodies obtained from one or more methods selected from the group consisting of:

(a) gel filtration,
(b) low conductivity precipitation,
(c) ion exchange column chromatography; and
(d) nanofiltration.

17. A pharmaceutical composition comprising an effective amount of human polyclonal antibodies against Zika virus, and at least one pharmaceutically acceptable excipient selected from the group consisting of a preservative, an antioxidant, a coating, an isotonic and absorption delaying agent, a surfactant, and a buffer.

18. The pharmaceutical composition of claim 17, wherein the human polyclonal antibodies do not contribute to Antibody Dependent Enhancement (ADE).

19. A method of reducing fetal mortality in a pregnant subject, or reducing a risk of a pregnant subject giving birth to a child having microcephaly, comprising administering to a pregnant subject in need thereof an effective amount of the pharmaceutical composition of claim 17.

20. A method of preventing, treating or ameliorating at least one symptom of Zika virus infection in a subject in need thereof, or of decreasing the frequency or severity of at least one symptom of Zika virus infection in a subject in need thereof, comprising administering the pharmaceutical composition of claim 17 to the subject.

21. The method of claim 1, wherein the composition further comprises at least one pharmaceutically acceptable excipient selected from the group consisting of a preservative, an antioxidant, a coating, an isotonic and absorption delaying agent, a surfactant, and a buffer.

* * * * *